United States Patent [19]

Sommer

[11] Patent Number: 4,979,822
[45] Date of Patent: Dec. 25, 1990

[54] PARTICLE MEASURING FLUID CELL HAVING NON-CORRODIBLE SHIMS

[75] Inventor: Holger T. Sommer, Greenbelt, Md.
[73] Assignee: Pacific Scientific Company, Newport Beach, Calif.
[21] Appl. No.: 358,564
[22] Filed: May 30, 1989
[51] Int. Cl.⁵ .............................................. G01N 1/10
[52] U.S. Cl. ..................................... 356/246; 356/338
[58] Field of Search ........................ 356/246, 338, 410
[56] References Cited

U.S. PATENT DOCUMENTS

| | | | |
|---|---|---|---|
| 3,805,187 | 4/1974 | Lempicki et al. | 331/94.5 |
| 4,260,258 | 4/1981 | Rose et al. | 356/246 |
| 4,844,611 | 7/1989 | Imahasha et al. | 356/246 |

Primary Examiner—Vincent P. McGraw
Assistant Examiner—S. A. Turner
Attorney, Agent, or Firm—Lane, Aitken & McCann

[57] ABSTRACT

A shim for use in defining a fluid passage in a particle detecting fluid cell has a base portion of metal and head portion, defining the fluid passage, which haws a metal core and a covering which is non-corrodible by water and acid. The sides of the covering and the base portion define continuous flat surfaces which are sandwiched between plates defining the other boundaries of the flow passage. The coverings form a fluid tight seal with the plates and the base portions of the shims bear the compressive forces exerted on the shims by the plates.

19 Claims, 2 Drawing Sheets

PARTICLE MEASURING FLUID CELL HAVING NON-CORRODIBLE SHIMS

BACKGROUND OF THE INVENTION

The present invention relates to a particle measuring fluid cell employed in a system to measure the size of particles entrained in a liquid stream or gas flowing through the cell and, more particularly, to shims which define a narrow passageway for the liquid through the cell.

Devices for measuring the size of particles entrained in a liquid stream, wherein the devices employ a collimated beam of light through a collimating lens system and a light sensitive element, are known in the prior art. Such a device is disclosed in U.S. Pat. No. 4,260,258 in the name of Dennis H. Rose et al. In the device disclosed therein, a particle measuring fluid cell includes a light source in the form of a light emitting diode, which projects a beam of light through a collimating lens system, across the fluid stream contained in a fluid flow channel and onto a light sensitive element. Particles carried by the fluid stream cast a shadow on the light sensitive element, which causes a change in the output signal level from the light sensitive element. By utilizing sensitive signal detectors, the change in the signal can be correlated with a given particle size, so that particles of various particle sizes can be measured and counted. In the region where the light beam intersects the fluid stream, a very narrow channel for the fluid stream is defined by a pair of shims sandwiched between flat plate members.

A problem arises from the fact that such particle measuring fluid cells are used for measuring particles in a wide variety of liquids and gases, such as water, strong acids and gaseous hydrochloride acid, having different corrosive characteristics. For measuring particles in water, the shims are made of stainless steel, but when the liquid is a strong acid, the shims must be made of platinum or some other expensive metal not corrodible by the acid. Thus, different devices employing parts of different materials must be made and stocked so that all applications of the devices can be satisfied. The problem is complicated by the fact that the fluids flowing through the cells are under high pressure.

As was mentioned above with connection with U.S. Pat. No. 4,260,258, the stainless steel is suitable for the shims of particle measuring fluid cells where the liquid is water, but unsuitable for some acids, which will corrode stainless steel. Shims made entirely of non-metallic materials have also been found to be unsatisfactory. The fluid pressure inherent in particle measuring fluid cells requires the shims to be sandwiched between the flat plate members under considerable compressive force. When the plates are made entirely of a relatively soft material, such as a plastic, the material of the plates cold flows under the large compressive forces exerted by the flat plate members. This cold flowing leads to leakage in the fluid cell and blockage of the flow passage.

SUMMARY OF THE INVENTION

By the present invention, particle measuring fluid cells of a single construction are suitable for use in all applications of the cells. This universality simplifies the manufacturing process, eliminates the need for storing various stock materials for use in different fluid cells, and avoids the need for the manufacturer and retailers to stock different types of completed fluid cells for different applications. In addition, corrosion protection for all applications is provided for the shims in the cells without a substantial increase in cost.

In order to provide the above advantages, shims for the particle measuring fluid cells, which are made of an incompressible material such as metal, are partially coated with a non-corrodible material which protects the shims, even against strong acids. The material of the coating can be a chlorotrifluoroethylene resin, for example, a chlorotrifluoroethylene resin known as KEL-F, a trademark of 3M Co. The shims include body portions and head portions, the head portions of two shims cooperating with one another to define the fluid flow passage in each fluid cell. Only the head portions are coated. The incompressible material of the head portions of the shims is both thinner and narrower than the base portions, thereby giving the incompressible material part of the head portions a smaller cross sectional area than the base portions. The head portions are coated with the non-corrodible material, and the sides of the coated shims are lapped so that the coating of the head portions and the incompressible material of the base portions define continuous flat surfaces which are engaged by side plates, which sandwich the shims to define the particle measuring fluid cell and to form fluid tight seals with the coating on the head portions. The incompressible material of the base portions determines the spacing between the plates and, thus, the width of the flow passage, and prevents cold flowing of the coating by bearing the compressive forces of flat plate members and by preventing those plate members from over-compressing the coating on the head portions.

Alternatively, the shims may be made entirely of corrosion resistant material when the application does not require a very high pressure. However, when such shims are used careful assembly is required. Also, a corrosion resistant material must be selected which is relatively resistant to deformation by cold flow.

DETAILED DESCRIPTION OF THE PREFERRED EMBODIMENTS

Figure 1:
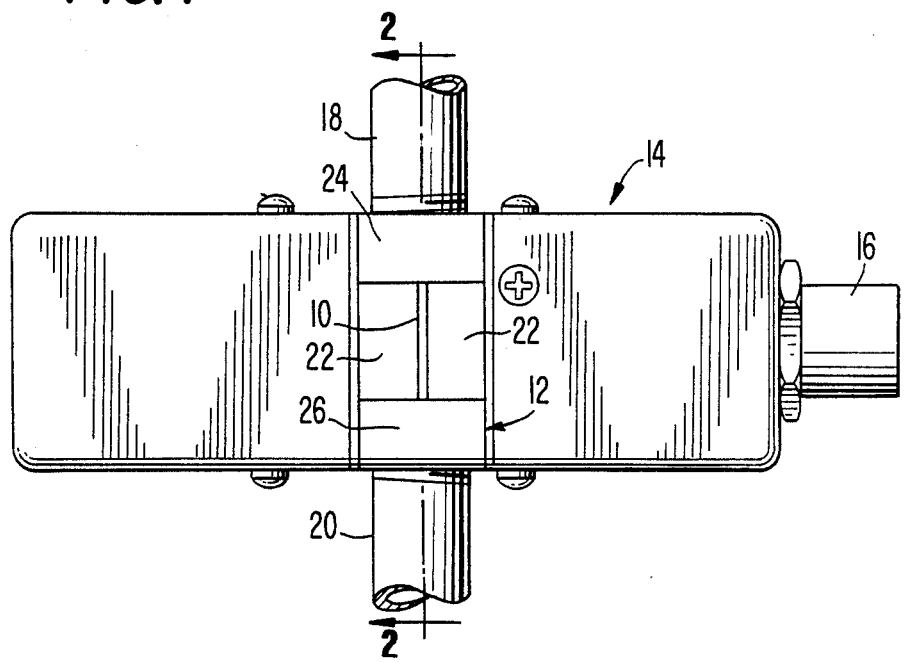
FIG. 1 shows a side elevation of a particle measuring fluid cell employing the shims according to the present invention combined in a block diagram with particle measuring circuitry.

As can be seen from FIG. 1, the shim according to the present invention, which is designated by the reference numeral 10, is included in a block assembly 12, which is positioned at the center of a particle measuring sensor 14 for detecting particles in a fluid stream. As disclosed in U.S. Pat. No. 4,260,258, a light source directs a light beam through the fluid stream within the sensor and a photodetector converts the light scattered by particles passing through the stream to pulses having amplitudes corresponding to the sizes of the particles. The particle measuring sensor 14 includes an end connector 16 by which the particle measuring sensor is connected to a power supply (not shown), and to particle measuring circuitry 17, an example of which is disclosed in U.S. Pat. No. 4,260,258. In a typical particle measuring sensor configuration, the output pulses are amplified to supply an amplified pulse signal to a threshold detector. The threshold detector supplies digital information to an output device, such as a numerical readout, which gives an indication of the number of particles of various size groupings measured by the particle measuring sensor 14. In addition, the average level output of the amplified pulse signal is supplied to an average level detector which controls the power supply so that the intensity of all light source used for measurement within the particle measuring sensor 14 can be maintained at a constant level using the average level of the amplified pulse light signal as a feed back signal.

A particle bearing fluid stream is fed under high pressure through the particle measuring sensor 14 typically by means of an inlet conduit 18 and an outlet conduit 20. In a common arrangement, the conduits 18 and 20 are part of a hydraulic circuit or gas supply system. The hydraulic circuit, for example, may be a hydraulic line in a machine employing plural hydraulic actuators. A small portion of the hydraulic flow from a pump in the hydraulic system is bypassed through the conduits 18 and 20 so that the particle measuring fluid cell 14 can be used to monitor the impurity level of the hydraulic fluid. This makes it possible for the operator of the hydraulic equipment to change the hydraulic fluid when the particle size and quantity of particles within the fluid reach a level which threatens to damage the system.

Figure 2:
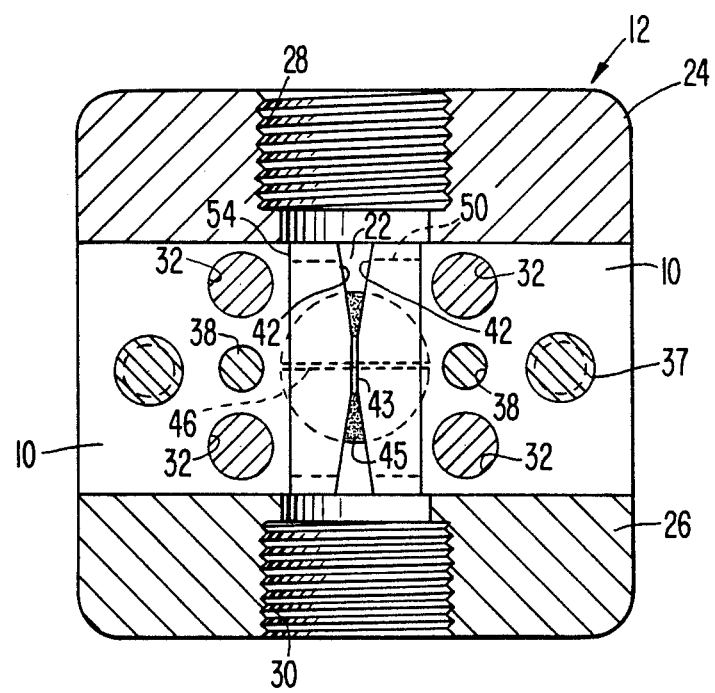
FIG. 2 is a cross section taken along the line 2—2 of the fluid cell of FIG. 1, with inlet and outlet conduits removed.
Figure 3:
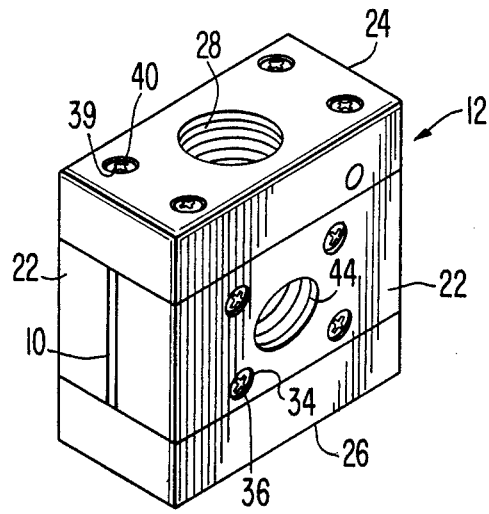
FIG. 3 is a perspective view of the block assembly from the center of the cell of FIG. 1.

As can be seen from FIG. 2, which is a cross section taken through the block assembly 12 along the line 2—2 in FIG. 1, and FIG. 3, a pair of the shims 10 are used in the block assembly 12. The shims are sandwiched between two plates 22, and the resulting subassembly is fixed between a pair of blocks 24 and 26 to define the block assembly 12, the blocks 24 and 26 engaging side edges of the shims 10 and sides of the plates 22. The blocks 24 and 26 have threaded ports 28 and 30, respectively, to permit the connection of the inlet conduit 18 and the outlet conduit 20. The shims 10 are provided with a plurality of openings 32, and the plates 22 include bores 34 (FIG. 3) aligned with the openings 32 so that screws 36 can be used to hold the plates 22 together, sandwiching the shims 10. Openings 37 are provided in the shims 10 to accept aligning pins when the shims are positioned on the plates 22. After alignment, the aligning pins are removed. Additional openings 38 are included in the shims 10, so that a precision tool can be inserted in the openings 38 of both shims 10 and the spacing between the shims can be set precisely in order to provide exact dimensions for the fluid flow passage. Bores 39 are provided in the blocks 24 and 26, and the plates 22 include bores (not shown) orthogonal to the bores 34 to permit the blocks 24 and 26 to be secured to opposite sides of the plates 22 by screws 40.

As can be seen from FIG. 2, the shims 10 have angled edges 42 which cooperate with one another, and with the plates 22, to define a narrow flow passage 43 for the fluid between the inlet port 28 and the outlet port 30. As examples of the thicknesses of the shims 10 and their spacing from one another in the particle measuring fluid cell 14, shims having a 1 mm. thickness can be spaced by 0.090 mm. 0.150 mm., or 0.400 mm. and shims having a 2.5 mm. thickness can be spaced 0.150 mm. or 0.400 mm. Each plate 22 has a central aperture 44 which is aligned with the central aperture 44 of the other plate, and a transparent window sapphire 45 is mounted in each central aperture, so that one surface of the window is flush with the shim-contacting surface of its associated plate 22. By this arrangement, the windows 45 define a portion of the flow passage for the fluid. A source of collimated light is positioned behind one of the windows 45, and a photodetector is positioned behind the other of the windows, so that a collimated light beam passes through one window 45, the fluid flow passage 43, and the other window before striking the photodetector. The window 45 behind which the light source is mounted is covered with an opaque material so that only a narrow slit 46 is left transparent through which the light beam can pass. Together, the slit 46 and the angled edges 42 of the shims 10 form a small, rectangular light path. Instead of using a slit, a collimated light beam may be focused into the cell center using a cylindrical lens arranged so that the focused beam covers the entire cross section of the fluid stream. All particles in the fluid must flow across the small light path and must affect the light beam. Therefore, all of the particles in the fluid are measured.

Figure 4:
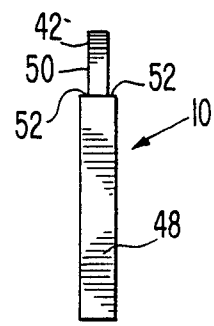
FIG. 4 is a side view of a shim according to the present invention with the corrosion protecting layer removed.

The shims 10 are basically unitary elements made of an incompressible material, such as stainless steel. As can be seen from the side view of FIG. 4, each shim 10 has a body portion 48 and a head portion 50. The head portion 50 is thinner than the body portion 48, thereby defining shoulders 52 where the body 48 meets the head 50. As can be seen from FIG. 2, the head portion 50 is also narrower than the body portion 48, that is, the head portion 50 has a smaller transverse dimension than the body portion 48, thereby defining shoulders 54. The relative smallness of the head portion 50 in two dimensions gives the head portion 50 a smaller cross sectional area than the body portion 48.

Figure 5:
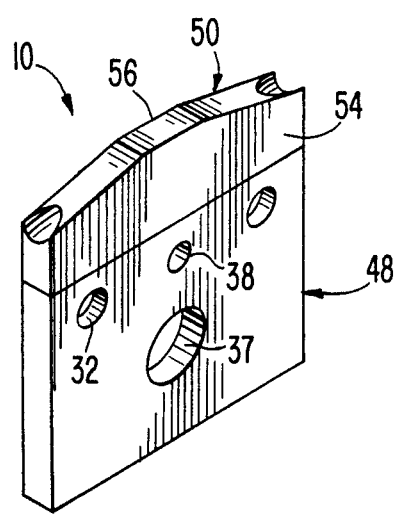
FIG. 5 is a perspective view of a shim according to the present invention with the corrosion protection layer in place.
Figure 6:
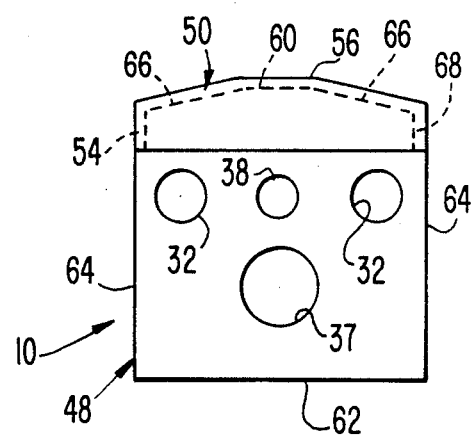
FIG. 6 is a front elevation of the shim of FIG. 5.

As can be seen from FIGS. 5 and 6, the head portion 50 is covered by another material 56, a non-corrodible material, which increases the cross sectional area of the shim 10 at its head portions 50 to equal the cross sectional areas of the body portion 48. The material 56 protects the shim 10 from corrosion by the fluid passing through the flow passage which the shims help define. Suitable plastic material, such as a chlorotrifluoroethylene resin, is contemplated for the covering 56, and a chlorotrifluorethylene resin known under the name KEL-F is one material which is particularly well suited. Another material suited for use as the covering 56 is available under the name KINAR, a trademark of Pennwalt. The covering 56 is applied as a coating on the head portion 50, and the shim 10 is then lapped on its sides which are to be sandwiched between the plates 22, in order to provide continuous flat surfaces, partly of metal and partly of resin, for such sandwiching. The pressure of the side plates 22 against the covering 56 on the head portions 50 of the shims 10 provides a fluid tight seal for the flow of the fluid through the narrow flow passageway 43 defined by the shims 10 and the plates 22. Depressions 58 are provided in the covering 56 at the corners of the head portion 50 to improve the flow characteristics of the fluid flowing through the particle measuring sensor 14, since the corners of the head portions 50 are located in the flow path of the fluid at the inlet and outlet ports 28 and 30 (FIG. 2). The incompressible material of the body portions 48 of the shims 10 determines the spacing between the plates 22 and, thus, the width of the flow passage 43, and prevents cold flowing of the covering 56 by bearing the compressive forces exerted on the shims 10 by the plates 22 and by preventing the plates 22 from overcompressing the covering 56.

As can be seen further from FIGS. 5 and 6, the angled edge 42 of each shim 10 includes a central portion 60 which is parallel to a bottom edge 62 of the shim 10 and perpendicular to side edges 64 of the shim. From ends of the central portion 60, beveled portions 66 extend to the side edges 68 of the head portion 50, which are parallel to the side edges 64 of the shims 10. The beveled portions 66 lie at a small angle with respect to the central portion 60, for example, 9 degrees. When the covering is applied, the same angle is maintained, and the central portion occupies about one-third of the total length of the covered head portion 50.

For lower pressure applications the shims may be made entirely of a corrosive resistant synthetic resin, such as pyromellitimide sold under the trademark VESPEL, which exhibits relatively good resistance to cold flowing at moderate pressures. With such shims, however, the sensor must be carefully assembled to insure that the plates 22 exert uniform pressure on the shims so that a good seal is achieved with reduced compressive force exerted on the shims by the plates 22 and to minimize any cold flowing tendency.

It is contemplated that various modifications of the specific embodiments described above may be described without departing from the spirit and scope of the invention, which is defined in the appended claims.

I claim:

1. A shim for defining a flow passage in a particle detecting fluid cell in cooperation with a like shim and with plates which place the shims in compression, wherein any of various fluids flow through the flow passage under pressure, comprising:
   a body portion having first and second sides, said body portion being made of an incompressible material having a first predetermined thickness;
   a head portion mounted on said body portion and having first and second sides, said head portion being made of incompressible material having a second predetermined thickness; and
   a covering on said head portion, said covering having a surface defining one side of said flow passage and contacting the fluid flowing through said flow passage, and being non-corrodible by the fluids flowing through the flow passage.

2. The shim of claim 1, wherein the covering is made of a chlorotrifluoroethylene resin.

3. The shim of claim 1, wherein said head portion has a top edge adapted to define the flow passage, and the covering includes a top portion covering said top edge and at least one side portion covering at least one of the first and second sides of said head portion.

4. The shim of claim 3, wherein said side portion of said covering defines a total thickness parallel to said second predetermined thickness of said head portion, said total thickness of said side portion of said covering and said second predetermined thickness of said head portion together being equal to said first predetermined thickness of said body portion.

5. The shim of claim 1, wherein the covering is a coating.

6. The shim of claim 1, wherein said body portion has side edges and a first width between said side edges, and said head portion has side edges and a second width between the side edges of said head portion, said second width being less than said first width.

7. The shim of claim 6, wherein said covering has end portions covering said side edges of said head portion.

8. The shim of claim 1, wherein the incompressible material is stainless steel.

9. A cell for measuring particles in a fluid flowing under pressure through the cell, comprising:
   a fluid inlet;
   a fluid outlet; and
   means defining a fluid passage between said inlet and said outlet, said fluid passage defining means comprising opposed plates and two shims positioned between said opposed pates and being spaced from one another, said shims having opposite sides contacted and placed under compression by said opposed plates;
   wherein each said shim includes:
      a body portion having first and second sides, said body portion being made of an incompressible material having a first predetermined thickness;
      a head portion mounted on said body portion and having first and second sides, said head portion being made of an incompressible material having a second predetermined thickness less than said first predetermined thickness; and
      a covering on said head portion, said covering having a surface defining one side of said flow passage and contacting the fluid flowing through said flow passage, and being non-corrodible by the fluids flowing through the flow passage.

10. The cell of claim 9, wherein the covering on said head portion is made of a chlorotrifluoroethylene resin.

11. The cell of claim 9, wherein the covering is a coating.

12. The cell of claim 9, wherein said body portion of each shim has side edges and a first width between said side edges and said head portion has side edges and a second width between the side edges of said head portion, said second width being less than said first width.

13. The cell of claim 12, wherein said second width and said covering together equal said first width.

14. The cell of claim 9, wherein the incompressible material is stainless steel.

15. The cell of claim 9, wherein the head portion of each said shim has a top edge adapted to define the flow passage, and the covering includes a top portion covering said top edge and at least one side portion covering at least one of the first and second sides of said head portion.

16. The cell of claim 15, wherein said side portion of said covering defines a total thickness parallel to said second predetermined thickness of said head portion, said total thickness of said side portion of said covering and said second predetermined thickness of said head portion together being equal to said first predetermined thickness of said body portion.

17. The cell of claim 9, wherein the covering of each said shim has end portions covering said side edges of said head portion.

18. A particle measuring system comprising cell for measuring particles in a fluid flowing under pressure through said cell, said cell having a fluid inlet, a fluid outlet means, and means defining a fluid passage between said inlet and outlet, said fluid passage defining means comprising opposed plates and two shims positioned between said opposed plates and being spaced from one another, said shims having opposite sides contacted and placed under compression by said opposed plates; wherein each of said shims has a surface contacted by the fluid flowing through said cell made of a pyromellitimide, and means to measure the size of particles entrained in a fluid stream passing through said fluid passage.

19. A cell is recited in claim 18 wherein said shims are made entirely out of pyromellitimide.

* * * * *

UNITED STATES PATENT AND TRADEMARK OFFICE
CERTIFICATE OF CORRECTION

PATENT NO. : 4,979,822

DATED : December 25, 1990

INVENTOR(S) : Holger T. Sommer

It is certified that error appears in the above-identified patent and that said Letters Patent is hereby corrected as shown below:

On the title page:
In the Abstract, line 3, "haws" should be --has--.

Column 6, line 17, "pates" should be --plates--.

Signed and Sealed this

Fourteenth Day of July, 1992

Attest:

DOUGLAS B. COMER

*Attesting Officer*    *Acting Commissioner of Patents and Trademarks*